United States Patent [19]

Meisner

[11] Patent Number: 4,772,591
[45] Date of Patent: Sep. 20, 1988

[54] METHOD FOR ACCELERATED WOUND HEALING

[75] Inventor: Lorraine F. Meisner, Madison, Wis.

[73] Assignee: Peritain, Ltd., Madison, Wis.

[21] Appl. No.: 852,522

[22] Filed: Apr. 16, 1986

Related U.S. Application Data

[63] Continuation-in-part of Ser. No. 778,811, Sep. 25, 1985, Pat. No. 4,647,453, which is a continuation-in-part of Ser. No. 662,069, Oct. 18, 1984, Pat. No. 4,590,067.

[51] Int. Cl.$^4$ .................... A61K 31/70; A61K 31/34; A61K 33/42; A61K 33/10
[52] U.S. Cl. .................................... 514/62; 424/128; 424/154; 424/156; 514/23; 514/474
[58] Field of Search ............... 514/825, 474, 154, 156, 514/62, 23; 424/128, 154, 156

[56] References Cited

U.S. PATENT DOCUMENTS 3,232,836  2/1966  Cariozzi et al. ................ 514/62
4,006,224  2/1977  Proddra ........................ 514/62

OTHER PUBLICATIONS

The Healing Factor—"Vitamin C" Against Disease, Irwin Stone–1972, pp. 178–179.
Tapadinhas, et al., Pharmatherapeutica, 3(3), 157–168 (1982).
Bekesi, et al., Cancer Research, 29, 353–359 (1969).
Laszlo, et al., Journal of the National Cancer Institute, 24, 267–281 (1960).
Litwin, Journal of Cell Science, 14, 671–80 (1974).
Kolata, Science, 219, 377–378 (Jan. 1983).
Jain, et al., Agents and Actions, 11(3), 243–249 (1981).
Gualano, et al., Pharmacological Research Communications, 15(7), 683–696, (1983 Jul.).
Thomas, et al., Journal of Pharmacy and Pharmacology, 26(2), 151–152, (Feb. 1974).
Borne, et al., Journal of Medicinal Chemistry, 15(12), 1325–1326, (Dec. 1972).
Hall, et al., Journal of Pharmaceutical Sciences, 69(12), 1451–1452 (Dec. 1980).
Kwapiszewski, et al., Arch. Immunol. Ther. Exp., 17(6), 729–731 (1979).
Coffey, et al., Advances in Cyclic Nucleotide Research, 9, 661–674 (1978).
Martin Stanisstreet, *J. Embryol. Exp. Morph.*, vol. 67, pp. 195–205, 1982.
S. G. Harvey and J. R. Gibson, *British Journal of Dermatology*, vol. III, Supplement 27, pp. 171–173, 1984.
L. A. Brunsting and D. G. Simonsen, *Journal A.M.A.*, Dec. 16, 1933, pp. 1937–1940.
W. M. Ringsdorf and E. Cheraskin, *Oral Surgery*, Mar. 1982, pp. 231–236.

*Primary Examiner*—Douglas W. Robinson

[57] ABSTRACT

A method and composition for accelerating the healing of wounds in animals and humans is disclosed. The method comprises administration of ascorbic acid, a source of biologically available calcium, a precursor or stimulant of epinephrine or nor-epinephrine selected from tyrosine and phenylalanine, and an anti-inflammatory substance selected from anti-inflammatory sugars, amino sugars and biocompatible acid addition salts thereof, and anti-inflammatory amino acids. Treatment in accordance with the present method reduces or prevents tissue degenerative effects of the inflammation associated with the natural wound healing process and promotes connective tissue (scar tissue) growth in the wound.

12 Claims, No Drawings

METHOD FOR ACCELERATED WOUND HEALING

CROSS REFERENCE TO RELATED APPLICATION

This application is a continuation in-part of pending U.S. application Ser. No. 06/778,811, filed Sept. 25, 1985, issued as U.S. Pat. No. 4,647,453 which application was a continuation-in-part of U.S. application Ser. No. 06/662,069 filed Oct. 18, 1984, issued as U.S. Pat. No. 4,590,067.

BACKGROUND AND SUMMARY OF THE INVENTION

The present invention relates to wound healing. More specifically it relates to a method for accelerating wound healing in humans and animals by administration of a combination of natural substances which cooperatively function to promote the body's physiological mechanism for repair of damaged body tissue.

A wound is tissue loss or damage anywhere in the body caused by physical or chemical means. Principle physical factors responsible for wounds are trauma and surgery. Wounds can also be caused by sources of chronic irritation and inflammation of body tissue.

Periodontal disease is an inflammatory disorder of the gums variously referred to as gum disease, periodontitis, and gingivitis. With the use of fluoride in drinking water and the daily use of toothpaste to help reduce tooth loss due to decay, gum disease has become the largest cause of tooth loss in the adult population of the United States, accounting for approximately 70% of such losses. The disorder results from the accumulation of plaque, particularly within the gum line, which, unless effectively removed, produces a chronic inflammatory process of the gingiva that spreads and destroys the connective tissues supporting the tooth as well as the tooth itself. Effective removal of plaque is difficult even with a vigorous and sustained program of brushing and flossing, and it has become clear that for effective control of periodontal disease, a more specific treating agent is needed.

Another inflammatory disease which effects degeneration of connective tissues is osteoarthritis. Although the cause of osteoarthritis is obviously different from periodontal disease, the pathogenesis is much the same: localized chronic inflammation with concomitant connective tissue degeneration. In periodontal disease, the body's response to the bacterial plaque results in an enzymatic attempt by the inflammatory cells to destroy the bacteria, and because this attack is non-specific it also destroys adjacent normal tissues of the host, thereby forming periodontal pockets which provide a niche for bacteria which are again attacked by inflammatory cells of the body to further erode the connective tissues surrounding the teeth. In osteoarthritis, the body's inflammatory response is localized in the joints. The body's inflammatory response is triggered by the presence of intracellular proteins released from the body's cells which have been injured or destroyed by wear and tear (or by injury in athletes) in skeletal joints. The body's inflammatory response leads to further erosion and tissue destruction, first wearing away connective tissues (cartilage) in the joint and then progressively the articular surfaces of the bones. Thus while periodontal disease and osteoarthritis are of radically different etiology, the pathogenesis of each parallels the other.

Wounds caused by trauma or surgery are also accompanied by an initial inflammatory response; it is a natural response of the body and the first step of the wound healing process. The initial inflammatory response is followed by the formation of fibrous tissue (scar tissue) specifically by proliferation of fibroblasts which produce collagen, mucopolysaccharides and gylcosaminoglycans at the wound site. Even thorgh surgical wounds are created aseptically, a certain amount of inflammation is required in the early healing stages in order to clear away the debris caused by the incision. It is important, though, to limit the inflammatory response so that the lack of specificity in release of proteolytic enzymes associated with the inflammatory response does not cause further damage to the host tissues. But again, a limited inflammatory response is essential to remove the debris which can provide a site for infection and/or chronic inflammation. Use of steroids, for example, so effectively inhibits inflammation that initial debris clearing process cannot be accomplished. For this reason steroids are not given post-operatively (except, of course, following transplants). On the other hand, less potent anti-inflammatory compounds such as amino sugars, including glucosamine, its chemical/biological analogues and certain anti-inflammatory amino acids such as cysteine and methionine are capable of physiologically limiting the inflammatory response, but not stopping it completely, so that optimal tissue repair process is possible. The second stage of wound healing involves a repair process which entails the influx and proliferation of fibrous tissue (fibroblasts) and the production of collagen and ground substance by the fibroblasts, resulting in the formation of dense fibrous connective tissue (scar).

It is therefore an object of this invention to provide a method for promoting wound healing in humans and animals.

Another more specific object is to provide a method for topical treatment of wounds to accelerate the wound healing process.

Other objects of the invention and its advantages over the prior art are apparent from the following description and claims.

DETAILED DESCRIPTION OF THE INVENTION

The present invention is grounded on applicant's discovery that the wound healing process can be favorably affected by administration of a composition comprising a mild anti-inflammatory agent and substances which in combination have been found to accelerate fibrous tissue growth, and scar tissue formation, essential to the healing process. Accelerated wound healing in accordance with this invention can be effected by oral administration of those substances. However, topical administration of those substances to a wound in a tissue compatible vehicle therefor is preferred. Where the wounded animal or human has an adequate dietary or dietary supplement intake of calcium in a biologically available form (about 10 to about 40 mg/kg) of body weight, the calcium component can be omitted optionally from the topical dosage form. While the present method is particularly directed at treatment of wounds in humans it finds parallel application for veterinary use.

The present method comprises the administration of four substances: a source of biologically available calcium; ascorbic acid; a precursor or stimulant of epinephrine or nor-epinephrine production selected from tyrosine and phenylalanine; and a mild anti-inflammatory substance selected from the anti-inflammatory members of the group consisting of simple sugars, amino sugars, amino acids, and derivatives thereof.

The calcium source can be administered independent of the other substances administered in accordance with the present method. The calcium source can be in the form of a dietary supplement or in the form of known dietary sources of biologically available calcium and should be administered in an amount sufficient to provide at least 10 milligrams of biologically available calcium per kilogram of body weight.

Periodontal disease can be viewed as a wound caused by chronic inflammation of the gums. A powder base having the following composition is useful for the treatment of existing periodontal disease:

| Parts by Weight | Component |
| --- | --- |
| 2 to 10 | Bone meal or similar calcium source |
| 1 to 5 | Glucosamine or other simple sugar or amino sugar having anti-inflammatory activity |
| 1 to 5 | Ascorbic acid |
| 0.5 to 2.5 | Tyrosine, phenylalanine, or other precursor or stimulant of epinephrine or nor-epinephrine production. |

In that composition bone meal, or the equivalent, serves as a source of calcium for tooth regeneration, as a general cleansing agent, and as a filler. Eguivalent substances include the art-recognized biologically compatible calcium salts, representative of which are calcium gluconate, calcium carbonate, tricalcium and dicalcium phosphate, dolomite and the like.

The calcium component is not critical to the efficacy of the composition utilized in accordance with this invention where the afflicted individual undergoing treatment is receiving adequate biologically available calcium through other calcium sources either in the form of calcium containing dietary supplements or simply by having adequate dietary sources of calcium in the diet. Dietary sources of calcium include milk, cheese, collard greens, canned sardines, tofu made with calcium salt, cooked spinach, ice cream, cottage cheese, cooked soybeans, cooked frozen broccoli, cooked legumes, eggs, and bread or other products made with milk or milk solids. An average adult requires between about 500 and 1500 milligrams/day of biologically available calcium. This can be translated into a calcium intake requirement of at least 10 milligrams of biologically available calcium per kilogram of body weight. Where a person or animal undergoing treatment in accordance with the present method has a daily calcium intake, either by dietary supplement or by normal dietary consumption of calcium containing foods, of between about 10 and about 25, or more preferably between about 15 and about 20 milligrams of biologically available calcium per kilogram of body weight, the calcium component can be omitted from topical formulations utilized in accordance with this invention.

Glucosamine, preferably used in the form of the salt with hydrochloric, sulfuric, phosphoric, or other biocompatible acid, is known to have an anti-inflammatory effect when taken orally or parenterally. Tapadinhas et al., *Pharmatherapeutica*, 3 (3), 157-168 (1982).

U.S. Pat. No. 3,232,836 describes a method for promoting healing by intravenous administration of large amounts 100-200 grams of glucosamine or salts thereof. U.S. Pat. No. 4,006,224 describes a method for treating ulcerative colitis by oral administration of D-glucosamine. Other sugars and sugar derivatives of similar activity include 2-deoxy-D-glucose, 2-deoxy-D-galactose, mannose, D-mannosamine, D-galactosamine, and the like. Bekesi et al., *Cancer Research*, 29, 353-359 (1969); Laszlo t al., *J. Natl. Cancer Inst.*, 24, 267-281 (1960); Bekesi et al., *J. Clinical Chem.*, 211, 3766-72 (1969). Also useful are glucosamine-6-phosphate, N-acetyl-D-glucosamine, N-acetyl-D galactosamine, uridine diphosphate (UDP) glucose, UDP-N-acetylglucosamine, and the like.

Ascorbic acid is disclosed in the scientific literature as useful in the treatment of many human/animal afflictions—from the common cold to periodontal disease. A study reported in 1964 showed that oral ingestion of ascorbic acid, combined with scaling of calculus from the periodontal disease sites, gave a greater increase in tooth stability than either treatment alone, both of which showed a small beneficial effect. El-Ashiry et al., *Int. Zeit. Vitaminforschung*, 34, 202-18, (1964). Dr. Irwine Stone summarized the therapeutic indications of ascorbic acid reported in the literature in his book *The Healing Factor "Vitamin C" Against Disease*, Grosset & Dunlap, New York (1972). Prior to the present invention, however, ascorbic acid has, to the best of our knowledge, never been used topically either alone or in any combination with other substances.

As a precursor of epinephrine, tyrosine is a preferred substance for use in the present invention. It has been shown in tissue culture to promote proliferation of the type of cell (fibroblasts) which are involved in the healing of periodontal tissue. Litvin, *J. Cell Science*, 14, 671-80 (1974). Activity of this sort is exhibited by both epinephrine and nor-epinephrine, and consequently by precursors and stimulants of epinephrine and nor-epinephrine synthesis.

The composition described hereinbelow is effective for the treatment and alleviation of tissue degenerative inflammations, including periodontal disease and for accelerating the healing of wounds caused by trauma or surgery. For preventing inflammatory disease or, after treatment has relieved such inflammatory condition which characterizes such disease, the composition is suitably modified by replacing the glucosamine or other anti-inflammatory, sugar or amino sugar with an amino acid having an anti-inflammatory effect. This substitution of an anti-inflammatory amino acid for glucosamine or other anti-inflammatory sugar or amino sugar can likewise be made in compositions used for accelerating wound healing in accordance with this invention. For this purpose, cysteine is preferred because it is bactericidal against *Streptococcus mutans* in addition to being anti-inflammatory in action. Other suitable amino acids include creatine, creatinine, L-tryptophan, valine, alanine, glycine, glutamine, aspartic acid, and S-methylcysteine, as well as the esters, N-benzenesulfonyl derivatives, and diazomethyl ketone and chloromethyl ketone analogs of the N-tosyl derivatives thereof, and the like. Jain et al., *Agents and Actions*, 11, 3 (1981); Gualano et al., *Pharmacol. Res Commun.*, Jul. 1983, 15(7), p. 683-96; Thomas et al., *J. Pharmacol.*, Feb. 74, 26(2), p. 151-2; Borne et al., *J. Med. Chem.*, Dec. 72, 15(12), p. 1325-6; Hall et al., *J. Pharm. Sci.*, Dec. 1980, 69(12), p.

1451-2; Kwapiszewski et al., *Arch. Immunol. Ther. Exp.* (Warsz.), 1979, 27(6), p. 729–31.

A composition useful for the treatment of tissue degenerative inflammatory disease in animals afflicted with such disease or disposed to development of such disease comprises, in parts per weight: ascorbic acid, 1 to 5 parts; a precursor or stimulant of epinephrine or nor-epinephrine production selected from tyrosine or phenylalanine, 0.5 to 2.5 parts; and an anti-inflammatory substance, 1 to 5 parts, said anti-inflammatory substance being selected from the amino sugars, glucosamine, D-mannosamine, D-galactosamine, their biocompatible acid addition salts, glucosamine-6-phosphate, N-acetyl-D-glucosamine, N-acetyl-D-galactosamine, UDP-N-acetylglucosamine; the sugars 2 deoxy-D-glucose, 2-deoxy-D-galactose and mannose; and the amino acids cysteine, creatine, creatinine, L-tryptophan, valine, alanine, glycine, glutamine, aspartic acid and S-methylcysteine. Where the composition is to be administered for the treatment of tissue degenerative inflammatory disease in animals whose normal dietary intake of calcium-containing food is not sufficient to provide an average of at least 10 milligrams of biologically available calcium for every kilogram of animal body weight, said composition should include, in addition, a calcium source providing 2 to 10 parts by weight biologically available calcium.

For treatment of periodontal disease the present composition can include optional ingredients, such as fluoride ion sources, sudsing agents, flavoring agents, sweetening agents, anti-calculus agents, anti-plaque agents, coloring agents, opacifying agents and the like, as described in Denny U.S. Pat. No. 4,254,101, which is incorporated herein by reference.

When prepared in the form of a powder useful for treatment of periodontal disease, the composition can be used by applying it with a soft toothbrush into the gingival-tooth junction twice per day, followed, if desired, by rinsing. It can also be used in the form of a paste or gel, in which the total concentration of the composition can be as low as about 5% by weight. For use in treating periodontal disease, the powder form is advantageously used, without dilution. The preventative formulation, for example with cysteine in place of glucosamine, can be used as a "matrix," blown in with a periojet at the time of surgery to promote healing and also to provide a better attachment for tissue. The composition for treatment of periodontal disease can be formulated as a toothpaste or a gel by milling in a conventional manner with an appropriate amount of glycerol, sorbital, and water, plus a thickening agent (for example, xanthan gum) to produce the desired consistency, plus an opacifying agent if the toothpaste form is desired. These formulations are used in a conventional manner with care to work the material into the ingival-tooth junction.

Osteoarthritis, a tissue destructive inflammatory disease characterized by a chronic inflammation of the connective tissue surrounding skeletal joints, is treated to reduce or prevent the tissue degenerative effects of the inflammatory disease and to promote connective tissue regrowth. This is accomplished by the oral administration of the following substances to an animal or person afflicted with such disease or disposed to the development of such disease, in the relative mass proportions indicated: ascorbic acid, 1 to 5 parts; biologically available calcium, 2 to 10 parts; a precursor or stimulant of epinephrine or nor-epinephrine selected from tyrosine and phenylalanine, 0.5 to 2.5 parts; and an anti-inflammatory substance, 1 to 5 parts, said anti-inflammatory substance being selected from the above-recited amino sugars, amino sugar derivatives and acid addition salts thereof, sugars, sugar derivatives and amino acids. Oral administration of those substances in the proportions indicated has also been found to accelerate wound healing. The biologically available calcium component can, as in the case of the above-described method for treatment of periodontal disease, be supplied through normal dietary consumption of foods containing biologically available calcium or by consumption of calcium-containing dietary supplements.

For wound healing in accordance with the present invention, topical application of the above described composition—with or without the calcium component depending on the patient's daily level of calcium ingestion as described above—is preferred. For such preferred topical administration, the composition can be formulated with a pharmaceutically acceptable tissue compatible, hydrophilic lotion-, ointment-, cream- or gel-base vehicle therefor. Such pharmaceutically acceptable vehicles are well-known in art and commercially available for formulation of active ingredients into a suitable form for topical application. The composition can constitute from about 1.0 to about 50%, more preferably about 3 to 50%, by weight of the formulation. The formulation can include, in addition to the components described hereinabove, other active ingredients, such as antibiotics, analgesics, anti-allergenics and the like. The formulation is preferably applied to the wound and adjacent tissue either as part of a wound dressing or as a lotion or cream to be rubbed on body tissue over and adjacent the wound. For optimum efficacy treatment in accordance with the presented method should be initiated as early as possible following occurrence of the wound. The formulation should be applied to the wound one to three times daily.

Where the above-defined substances are administered orally in accordance with the present method, they can be administered in combination in an uniform oral dosage formulation including the substances (with or without calcium depending on the person's or animal's existing diet) in the relative mass proportions indicated. The substance mixture can be formulated into a pharmaceutically acceptable dosage form for oral ingestion for example, powder, tablet or capsules using art-recognized drug formulation techniques. Such dosage forms can contain from about 250 milligrams to about 1,000 milligrams of the substance mixture. Alternatively each of the substances can be formulated individually into dosage forms suitable for oral administration and said individual dosage forms can be administered in combination in amounts effective to reduce or prevent the tissue degenerative effects of the inflammatory disease and to promote healing of wounds associated therewith. Thus, for example, treatment of osteoarthritis in a person or animal afflicted with such disease or disposed to the development of such disease can be accomplished by the method comprising daily oral administration of about 300 to about 2,000 milligrams of ascorbic acid, a calcium source providing from about 500 to about 1,500 milligrams of biologically available calcium; from about 250 milligrams to about 1,000 milligrams of tyrosine or phenylalanine and from about 300 milligrams to about 2,000 milligrams of a mild anti-inflammatory substance as defined hereinabove. Alternatively, preferred dosage levels on a mg/Kg of body weight basis are: ascorbic acid, about 5 to about 25 mg/Kg, more preferable about 10 to about 20 mg/Kg; biologically available calcium, about 10 to about 40 mg/Kg, more preferably about 15 to about 30 mg/Kg; tyrosine or phenylalanine, about 3 to about 15 mg/Kg, more preferably about 5 to about 10 mg/Kg; and an anti-inflammatory substance as disclosed hereinabove, about 5 to about 25 mg/Kg, more preferably about 10 to about 20 mg/Kg. Like oral dosage ranges are effective to promote healing of wounds caused by trauma or surgery in humans and animals.

The preferred daily dose for any particular animal or person afflicted with osteoarthritis would depend on the degree to which the disease has progressed at the time treatment is initiated. Thus for preventative purposes in individuals who have perhaps had past occurrences of the disease or, for example, in the case of athletes who subject their joints to continual stress and strain thereby initiating a potentially progressive inflammatory situation, dosages at the lower end of the above-cited dosage ranges are appropriate. In cases of advanced osteoarthritis, on the other hand, dosages in the mid to upper portions of the above described dosage ranges would be appropriate. Moreover, in cases of advanced osteoarthritis the present composition and method is advisably used in combination with an art-recognized non-steroidal analgesic/anti-inflammatory agent such as aspirin, ibuprofen, fenoprofen calcium, tolmetin sodium, indomethacin, piroxicam, naproxen and sulindac.

The invention is further illustrated in the following examples, none of which are to be construed as limiting the invention in any respect.

Examples 1–3 below exemplify compositions useful in accordance with the present invention.

EXAMPLE 1

| Powder formulation: | |
|---|---|
| Bone meal | 44% |
| Glucosamine | 22% |
| Ascorbic Acid | 22% |
| Tyrosine | 12% |
| | 100% |

EXAMPLE 2

| Powder formulation: | |
|---|---|
| Calcium gluconate | 40% |
| Mannose | 25% |
| Ascorbic Acid | 20% |
| Phenylalanine | 15% |
| | 100% |

EXAMPLE 3

| Powder formulation: | |
|---|---|
| Bone meal | 45% |
| Cysteine | 20% |
| Ascorbic Acid | 23% |
| Tyrosine | 12% |
| | 100% |

Examples 4 and 5 illustrate formulations of the composition of Example 1 for use in treatment of periodontal disease.

EXAMPLE 4

| Gel formulation: | |
|---|---|
| Powder, Example 1 | 6% |
| Sorbitol (70% aqueous) | 64 |
| Glycerol | 23 |
| Xanthan gum | 0.25 |
| Carboxyvinyl polymer | 0.25 |
| Sodium dodecyl sulfate | 1.5 |
| Flavor, q.s. | |
| Color, q.s. | |
| Water | 5 |
| Phosphate buffer to pH 7 | |
| | 100% |

EXAMPLE 5

| Toothpaste formulation: | |
|---|---|
| Powder, Example 1 | 20% |
| Sorbitol (70% aqueous) | 42.5 |
| Precipitated silica | 17 |
| Glycerol | 15 |
| Xanthan gum | 0.25 |
| Carboxyvinyl polymer | 0.25 |
| Sodium dodecyl sulfate | 1.0 |
| Flavor, q.s. | |
| Water | 4.0 |
| Phosphate buffer to pH 7 | |
| | 100% |

The following example reports the results of a clinical study of a composition or the present invention in the treatment of advanced periodontal disease.

EXAMPLE 6

The patients in this study had all been referred for periodontal surgery because of advanced disease. Selection for the study was conditioned on two factors: (1) no immediate necessity for the surgery; and (2) willingness to learn to use the required brushing technique, as described in the publication "The Realistic Way to Dental Wellness," by John H. Duffy, D.D.S., Realistic Hygiene, Inc., 2354 Highway AB, McFarland, Wis. 53558, U.S.A. (1978). Parallel groups of controls and test patients were selected on the basis of being as clinically similar as possible. As exceptions, two patients were chosen who had earlier refused to have surgery and had been "dry" brushing (without dentifrice or any other material added to the mouth) with proper technique under periodontal supervision for eighteen months and two years, respectively, without such impact on their disease. These two patients were chosen as test patients to study the beneficial effects of brushing alone as compared with short-term use of the powder of the present invention.

Both control and test patients practiced "dry" brushing for a minimum of three weeks to assure that they were using the proper brushing techniques, acceptable to the periodontist conducting the study. After the initial period, in which brushing techniques were evaluated and mistakes corrected, the controls were instructed to continue brushing twice a day, while the test patients were told to brush twice daily using a powder having the following composition:

| Bone meal | 4.6 parts by weight |
|---|---|
| Glucosamine | 2.8 |

| -continued | |
|---|---|
| Ascorbic acid | 3.2 |
| Tyrosine | 1.0 |

Progress was measured by using a University of Wisconsin periodontal probe to measure any difference in "pocket" depth from the beginning of the study until its conclusion. The "pockets" is the space between gum and tooth in periodontal disease which does not exist in healthy gums, providing a site for bacterial infection and inflammation which destroys the surrounding gum and osseous support for the tooth, and eventually causes the tooth itself to be lost. Pocket depth measurements were made on four sides of each tooth. All four readings for each tooth were then added together for all of the teeth of a given patient, and the result was divided by the total number of the patient's teeth (varying from patient to patient) to give an average score per tooth for the sum of the pocket depths on the four sides. A decrease in average pocket depth thus would represent an improvement in the patient's condition and a positive response to the treatment being employed.

Because brushing is a one-handed operation, usually done with the same hand by a given patient, the brushing tends to be more effective on the side opposite the brushing hand, with the result that periodontal disease tends to be less advanced on that side. For the same reason, the treatment carried out in the present invention also tends to by unsymmetrical. Because of this effect, data were accumulated separately for the left and right sides of the patients' mouths in order to rule out any resulting bias in the results.

As the accompanying tables show, there is no consistent relationship between the effects of proper brushing alone and time of brushing, with some patients showing considerable improvement while others showed deterioration. Indeed, in the control group there was not even a good correlation in the results on each side of the mouth, except that the left side averaged a greater improvement, as could be expected since the subjects were right-handed. On the other hand, in the test group no patient got worse, and the average decrease in pocket depth was approximately tenfold that seen with brushing along. In addition, slightly greater improvement was seen on the right side, suggesting that the powder had compensated for the effects of unequal brushing.

During the course of this trial, all patients were evaluated at frequent intervals (every three weeks or so) to make sure that their conditions did not worsen, which would have made immediate surgery necessary.

One patient (MS-C) had already had surgery on the right side of her mouth and wished to delay the surgery on the left side. She was put on the powder; after only one month of brushing with the powder, she improved so dramatically that surgery on the left side may no longer be necessary.

MS(A) was the first patient in the study, and several different proportions of ingredients in the powder were tested on him until an optimum formulation was found, as judged by a maximum suppression of inflammation. This was the formulation thereafter used on MS(A) and adopted for all of the other patients in the study. The time shown below in Tables 3 and 4 for MS(A)'s use of the powder are for his use of the optimum formulation, and, to simplify comparisons, all improvements achieved prior to MS(A)'s use of the final formulation are ascribed (inaccurately) to "brushing alone" —i.e., "dry" brushing. Thus, for MS(A), the improvement attributed to four months of brushing alone actually included two months of brushing with powder having varying proportions of ingredients. To avoid this inaccuracy, the results of the study are also reported at the bottom of Tables 3 and 4 without the data from MS(A). This more critical treatment of the data demonstrates even more impressively the effect of the powder on periodontal disease.

Although the only parameter which could be objectively quantified here was pocket depth, it was noted that the degree of grossly observable inflammation decreased in parallel with the degree of decrease in pocket depth.

In summary, the results of this clinical trial show that the powder formulation employed is effective in the treatment of periodontal disease, either to decrease inflammation prior to surgery or, in some cases, to even replace surgery.

TABLE 1

CONTROLS
Left Side of Mouth

| Subjects | Duration of Brushing (months) | Average Pocket Depth (mm) (Sum, 4 sides per tooth) | | |
|---|---|---|---|---|
| | | Before Brushing | After | Difference |
| JR | 3¼ | 13.14 | 13.50 | +0.36 |
| DB | 1¾ | 11.93 | 11.86 | −0.07 |
| DG | 2¼ | 11.76 | 11.15 | −0.61 |
| CM | 2½ | 13.54 | 13.62 | +0.08 |
| AS | 3¾ | 11.64 | 9.69 | −1.95 |
| SS | 3 | 9.23 | 8.15 | −1.08 |
| RT | 2¾ | 8.27 | 9.00 | +0.73 |
| | | | Average | −0.36 |

TABLE 2

CONTROLS
Right Side of Mouth

| Subjects | Duration of Brushing (months) | Average Pocket Depth (mm) (Sum, 4 sides per tooth) | | |
|---|---|---|---|---|
| | | Before Brushing | After | Difference |
| JR | 3¼ | 14.73 | 14.14 | −0.59 |
| DB | 1¾ | 13.33 | 13.75 | +0.42 |
| DG | 2¼ | 13.14 | 13.07 | −0.07 |
| CM | 2½ | 13.00 | 13.71 | +0.71 |
| AS | 3¾ | 12.50 | 10.50 | −2.00 |
| SS | 3 | 8.92 | 8.00 | −0.92 |
| RT | 2¾ | 9.16 | 9.33 | +0.17 |
| | | | Average | −0.26 |

TABLE 3

TEST PATIENTS
Left Side of Mouth

| Sub-jects | Duration (months) Brushing Alone | Duration (months) Brushing + Powder | Average Pocket Depth(mm) (Sum, 4 sides per tooth) Before Any Treatment | Average Pocket Depth(mm) After Brushing Alone | Average Pocket Depth(mm) After Brushing + Powder | Difference After Brushing Alone | Difference After Brushing + Powder | After Both |
|---|---|---|---|---|---|---|---|---|
| GG | 1 | 2 | 14.62 | 12.77 | 11.92 | −1.85 | −0.85 | −2.70 |
| NH | 1½ | 2 | 8.89 | 8.07 | 7.43 | −0.82 | −0.64 | −1.46 |
| RM* | 18 | 1½ | 16.43 | 13.57 | 11.57 | −2.86 | −2.00 | −4.86 |
| MR | 1¼ | 2 | 10.00 | 10.89 | 8.64 | +0.89 | −2.25 | −1.36 |
| MS(A) | 4 | 4 | 11.62 | 7.31 | 6.69 | −4.31 | −0.62 | −4.93 |
| MS(B) | 1½ | 2 | 13.66 | 13.50 | 10.43 | −0.16 | −3.07 | −3.23 |
| MS(C) | 5 | 1 | 12.86 | 10.57 | 8.64 | −2.29 | −1.93 | −4.22 |
| MS(D) | 24 | 1½ | 13.85 | 11.00 | 9.00 | −2.85 | −2.00 | −4.85 |
| | | | | | Average: | −1.78 | −1.67 | −3.45 |
| | | | | Average, excluding MS(A): | | −1.42 | −1.82 | −3.24 |

*RM and MS(D), prior to the beginning of this study, had declined surgery and were treated by "dry" brushing for the periods shown. When the composition ("powder") of the present invention became available, their brushing was continued with the powder. The results permit a comparison of the improvement provided by short-term brushing with the powder versus long-term brushing without.

TABLE 4

TEST PATIENTS
Right Side of Mouth

| Sub-jects | Duration (months) Brushing Alone | Duration (months) Brushing + Powder | Average Pocket Depth(mm) (Sum, 4 sides per tooth) Before Any Treatment | Average Pocket Depth(mm) After Brushing Alone | Average Pocket Depth(mm) After Brushing + Powder | Difference After Brushing Alone | Difference After Brushing + Powder | After Both |
|---|---|---|---|---|---|---|---|---|
| GG | 1 | 2 | 16.15 | 14.85 | 12.77 | −1.30 | −2.08 | −3.38 |
| NH | 1½ | 2 | 10.07 | 8.64 | 7.79 | −1.43 | −0.85 | −2.28 |
| RM* | 18 | 1½ | 14.36 | 12.29 | 10.71 | −2.07 | −1.58 | −3.65 |
| MR | 1¼ | 2 | 11.21 | 11.86 | 8.57 | +0.65 | −3.29 | −2.64 |
| MS(A) | 4 | 4 | 10.92 | 7.25 | 6.25 | −3.67 | −1.00 | −4.67 |
| MS(B) | 1½ | 2 | 14.29 | 14.70 | 11.00 | +0.41 | −3.70 | −3.29 |
| MS(C)** | | | | | | | | |
| MS(D)* | 24 | 1½ | 14.07 | 10.07 | 9.71 | −4.00 | −0.36 | −4.36 |
| | | | | | Average: | −1.63 | −1.84 | −3.47 |
| | | | | Average, excluding MS(A): | | −1.29 | −1.98 | −3.27 |

*RM and MS(D), prior to the beginning of this study, had declined surgery and were treated by "dry" brushing for the periods shown. When the composition ("powder") of the present invention became available, their brushing was continued with the powder. The results permit a comparison of the improvement provided by short-term brushing with the powder versus long-term brushing without.
**MS(C) is not included because she had received surgery on the right side of her mouth. Only the left side of the mouth was treated with powder.

The following examples 7-11 illustrate application to the treatment of osteoarthritis.

EXAMPLE 7

An Old English Sheepdog was born with congenital hip dysplasia (which improved upon splinting), developed severe secondary degenerative osteoarthritis when she was five years old, resulting in significant apparent pain on walking and an inability to run or jump. An x-ray of her pelvis revealed severe joint degeneration and advanced osteoarthritis. She was started on one aspirin per day, which appeared to offer some relief from pain but the dog's movements were still very limited. By the time the dog was seven years old she was severely lame. The dog was started on a daily dose of 250 mg tyrosine, 100 mg vitamin C, and 500 mg glucosamine. No calcium supplement was used since the dog received a bone meal supplement in her diet. After six months on that treatment the dog was able to move without pain. After three years on the medication she was completely ambulatory, with her only limitation being lateral movement of her rear legs. There was some apparent stiffness consistent with connective tissue growth supporting the femur in the greatest weight bearing area. An x-ray of the animal taken after three years showed that while there was little change in bony degradation, therefore indicating that the reversal of symptomology was due to the ingrowth of dense connective tissue growth in and around the afflicted joints.

During the second year the vitamin C/tyrosine/-glucosamine supplement was withheld for several days to see if it was necessary to be taken on a daily basis. After two days the dog began showing pain reguiring that the supplement be immediately reinstituted. Also, because of the advanced stage of her disease, the single aspirin a day was continued throughout treatment with the supplement.

EXAMPLE 8

A 66 year old woman with osteoarthritis of the cervical spine, secondary to osteoporosis had been experiencing severe pain for almost a year. She was treated in accordance with the present method by daily oral administration of the following substances: 500 mg tyrosine, 1000 mg vitamin C, 1000 mg glucosamine, and 1500 mg calcium carbonate. After six months on this regimen (which also included 3–600 mg Nalfon® tablets daily) she showed so much improvement that the dosage was decreased by one-half for the next two months. After that time she was completely free of pain and no longer took the Nalfon. She has remained completely symptom-free for two years following termination of treatment in accordance with the present invention.

EXAMPLE 9

A 73 year old man with diagnosed osteoarthritis of the spine and right hip had been taking non-steroidal anti-inflammatory medications for two years (first Motrin, then Naproxyn, when Feldene). However, his condition deteriorated so much and his pain was so great that he was unable to have his apartment. He began taking daily in combination 500 mg tyrosine, 1000 mg glucosamine, and 1000 mg vitamin C. He maintained a high calcium diet. After taking the composition for a year together with a standard non-steroidal anti-inflammatory medication (Nalfon, 1200 mg/day) he became completely symptom-free, and remained symptom-free for a period of six months following the time he stopped taking the substances in accordance with this method. Upon reoccurrence of his discomfort he resumed treatment in accordance with the present method and after three weeks was once again symptom-free.

EXAMPLE 11

A 53 year old woman was diagnosed as having osteoarthritis of the right hip and given standard non-steroidal anti-inflammatory therapy (Nalfon, 300 mg, 4 times per day). Although she initially experienced subjective improvement, some six months later her condition deteriorated to the extent that 600 mg Nalfon, four times daily, was required for function, but she was still in considerable pain and unable to walk without a severe limp. Nine months after the original diagnosis, x-rays of her pelvis revealed complete destruction of the cartilage in her hip so that bone was rubbing on bone; this was responsible for her severe symptomology. She was told that the only relief for her advanced disease was total hip replacement. While contemplating surgery, she began to take the present composition in the highest daily dose which applicant would recommend in accordance with the present method (1000 mg tyrosine, 2000 mg vitamin C, 2000 mg glucosamine and 1500 mg calcium carbonate in addition to a high calcium diet). After three days on this composition she began to experience slight pain relief, after one month considerable pain relief and significantly increased mobility, and after two months pain was diminishing to the point where she began to lower her Nalfon dose. She now walks without a limp, but after five months, still requires treatment in accordance with the present method in addition to 3–600 mg Nalfon daily.

EXAMPLE 12

Surgical wound healing

A 10 inch long surgical scar following total hip replacement was treated after suture removal (3 weeks post surgery) with the following formulation: 10% (by weight) tyrosine, 20% ascorbic acid, 20% glucosamine, +50% Dermabase (a commercial preparation in cream form which is used for carrying chemicals into and through the skin.). Since the subject was taking high doses of calcium orally, a calcium source was omitted from the formulation. The formulation was applied topically once daily to the top 5 inches of the wound. Aloe vera was applied to the other half of the wound (control). After one week, the formulation-treated half of the wound appeared lighter in color and the edges appeared more closely approximated than those in the control half. After three weeks, the difference between the two halves was so marked the subject refused to use the control (aloe vera), and began applying the formulation on the entire surgical wound. Although there was some improvement thereafter in the control portion of the wound even after another month of treatment it was still darker and more rough-edged than the half of the incisional wound treated with the formulation from the start of the study. This indicates that the formulation had been applied too late for optimal effect (i.e. that for optimal effect the formulation should be applied with the first month after surgery). This example also illustrates that despite adequate dietary calcium (which, even by itself, has been shown to be very important for wound healing), the topical application of the other three ingredients was required for optimal healing. There was a marked difference between the formulation-treated half of the wound and the aloe vera treated (control) half.

EXAMPLE 13

Healing of Chronic Inflammatory Lesion

A 33 year old male had chronic interstitial cystitis of two years duration, which began following an infection. Although he had been receiving all state-of-the-art treatments (including 8 surgical dilations and multiple cystoscopies), after two years his condition had deteriorated to the point that urinary frequency of two to three hours was interfering with his sleep, dysuria was so severe that he frequently required narcotics, and because of the almost continuous pain, sexual relations were no longer possible. The subject initiated a daily regimen consisting of oral administration of the following: 1500 mg glucosamine, 1500 ascorbic acid, and 1000 mg tyrosine. Due to a high dietary intake of calcium, supplemental calcium was judged not to be necessary. After one week on this regimen, all symptoms had improved, especially urinary frequency and dysuria. After 3 weeks on this regimen, he no longer had nocturia, urinary frequency had greatly diminished, his pain was so decreased that only an occasional acetaminophen was necessary for comfort, and he was able to resume a normal sex life for the first time in two years.

I claim:

1. A method for accelerating wound healing in an animal or human having a wound in body tissue caused by trauma or surgery, which method comprises administration of the following substances in the relative weight proportions indicated:
   ascorbic acid, 1 to 5 parts;
   biologically available calcium, 2 to 10 parts provided by a calcium source selected from the group consisting of bone meal, biologically compatible calcium salts and calcium-containing foods;
   a precursor or stimulant of epinephrine or norepinephrine selected from tyrosine and phenylalanine, 0.5 to 2.5 parts; and
   an anti-inflammatory substance, 1 to 5 parts, said anti-inflammatory substance being selected from the amino sugars glucoomine, D-mannosamine, D-galactosamine, their biocompatible acid addition salts, glucosamine-6-phosphate, N-acetyl-D-gluccasmine, N-acetyl-D-galactosamine, and UDP-N- acetylglucosamine, the sugars 2-deoxy-D-glucose, 2-deoxy-D-galactose and mannose, and the amino acids cysteine, creatine, creatinine, L-tryptophan, valine, alanine, glycine, glutamine, aspartic acid, and S-methylcysteine;

in which method the ascorbic acid, the phenylalanine or tyrosine, and the anti-inflammatory agent are administered topically and the calcium source is administered orally or topically in amounts effective to reduce or prevent tissue degenerative effects of wound-stimulated inflammation and to promote connective tissue growth.

2. The method of claim 1 wherein the administration of the biologically available calcium is provided by the animal's daily ingestion of substances selected from calcium-containing foods, bone meal and biologically compatable calcium salts in an amount sufficient to provide an average of at least 10 milligrams of biologically available calcium for every kilogram of animal body weight.

3. The method of claim 1 wherein the precursor or stimulant of epinephrine or nor-epinephrine is tyrosine.

4. The method of claim 3 wherein the anti-inflammatory substance is an amino acid.

5. The method of claim 4 wherein the anti-inflammatory agent is cysteine

6. The method of claim 3 wherein the anti-inflammatory agent is glucosamine or a biocompatible acid addition salt thereof.

7. The method of claim 1 wherein the source of biologically available calcium is selected from bone meal and biologically compatible calcium salts.

8. The method of claim 7 wherein the ascorbic acid, the source of biologically available calcium, the precursor or stimulant of epinephrine or nor-epinephrine and the anti-inflammatory substance are applied to the wound typically in a tissue compatible vehicle therefor.

9. The method of claim 8 wherein the precursor or stimulant of epinephrine or nor-epinephrine is tyrosine.

10. The method of claim 9 wherein the anti-inflammatory substance is an amino acid.

11. The method of claim 10 wherein the anti-inflammatory agent is cysteine.

12. The method of claim 9 wherein the anti-inflammatory agent is glucosamine or a biocompatible acid addition salt thereof.

* * * * *

UNITED STATES PATENT AND TRADEMARK OFFICE
CERTIFICATE OF CORRECTION

PATENT NO. : 4,772,591

DATED : September 20, 1988

INVENTOR(S) : Lorraine F. Meisner

It is certified that error appears in the above-identified patent and that said Letters Patent is hereby corrected as shown below:

At column 2, line 10, please delete "thorgh" and insert therefor --though--;

At column 2, line 60, please delete "adeguate" and insert therefor --adequate--;

At column 3, line 33, please delete "Eguivalent" and insert therefor --Equivalent--;

At column 4, line 10, please delete "t al.," and insert therefor --et al.,--;

At column 5, line 55, please delete "ingival-tooth" and insert therefor --gingival-tooth--;

At column 8, line 51, please delete "such" and insert therefor --much--;

At column 11, in Table 3, please delete "MS(D)" and insert therefor --MS(D)*--;

At column 12, line 55, please delete "reguiring" and insert therefor --requiring--;

UNITED STATES PATENT AND TRADEMARK OFFICE
CERTIFICATE OF CORRECTION

PATENT NO. : 4,772,591

DATED : September 20, 1988

INVENTOR(S) : Lorraine F. Meisner

It is certified that error appears in the above-identified patent and that said Letters Patent is hereby corrected as shown below:

At column 13, line 15, please delete "have" and insert therefor --leave--;

At column 14, line 66, please delete "glucoomine" and insert therefor --glucosamine--; and At column 16, line 15, please delete "typically" and insert therefor --topically--.

Signed and Sealed this

Eighteenth Day of April, 1989

Attest:

DONALD J. QUIGG

*Attesting Officer*  *Commissioner of Patents and Trademarks*